United States Patent
Kube et al.

(10) Patent No.: US 10,424,975 B2
(45) Date of Patent: Sep. 24, 2019

(54) SENSOR MODULE AND KIT FOR DETERMINING AN ANALYTE CONCENTRATION

(71) Applicant: Roche Diabetes Care, Inc., Indianapolis, IN (US)

(72) Inventors: Oliver Kube, Worms (DE); Michael Orth, Grossniedescheim (DE)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 313 days.

(21) Appl. No.: 15/249,642

(22) Filed: Aug. 29, 2016

(65) Prior Publication Data
US 2017/0055890 A1 Mar. 2, 2017

(30) Foreign Application Priority Data
Sep. 2, 2015 (EP) .................................... 15183461

(51) Int. Cl.
*H02J 50/80* (2016.01)
*A61B 5/00* (2006.01)
(Continued)

(52) U.S. Cl.
CPC ............ *H02J 50/80* (2016.02); *A61B 5/0002* (2013.01); *A61B 5/145* (2013.01);
(Continued)

(58) Field of Classification Search
CPC ... A61B 5/14503; A61B 5/145; A61B 5/0002; A61B 5/14532; A61B 5/746;
(Continued)

(56) References Cited

U.S. PATENT DOCUMENTS 6,360,888 B1  3/2002  McIvor et al.
7,756,561 B2  7/2010  Reggiardo et al.
(Continued)

FOREIGN PATENT DOCUMENTS

EP  1 850 226 A1  10/2007
EP  1011804 B1  8/2009
(Continued)

OTHER PUBLICATIONS

International Standard ISO/IEC 14443-2; Identification cards—Contactless integrated circuit cards—Proximity cards—Part 2: Radio frequency power and signal interface (Preview)(Jul. 15, 2016) (6 pages).
(Continued)

*Primary Examiner* — Eric F Winakur
*Assistant Examiner* — Abid A Mustansir
(74) *Attorney, Agent, or Firm* — Bose McKinney & Evans LLP (57) ABSTRACT

A sensor module (112) for determining a concentration of at least one analyte in a body fluid of a user is disclosed. The sensor module (112) includes at least one sensor element (116) adapted to determine the concentration of the analyte, wherein the sensor element (116) is at least partly implantable into a body tissue of the user; at least one control device (118) connected to the sensor element (116), wherein the control device (118) includes at least one data collection device (122) adapted to collect measurement data acquired by using the sensor element (116). The control device (118) further includes at least one wireless near-field communication device (124) adapted to transmit measurement data. The control device (118) further includes a rechargeable energy storage device (134) and is adapted to transmit at least one demand for recharging the rechargeable energy
(Continued)

storage device (134) via the near-field communication device (124).

16 Claims, 2 Drawing Sheets

(51) Int. Cl.
| | |
|---|---|
| *A61B 5/145* | (2006.01) |
| *H02J 7/02* | (2016.01) |
| *H02J 50/10* | (2016.01) |
| *H02J 50/20* | (2016.01) |
| *H02J 50/05* | (2016.01) |
| *H04B 5/00* | (2006.01) |
| *H02J 7/00* | (2006.01) |

(52) U.S. Cl.
CPC .......... *A61B 5/14532* (2013.01); *H02J 7/025* (2013.01); *H02J 50/05* (2016.02); *H02J 50/10* (2016.02); *H02J 50/20* (2016.02); *A61B 2560/0204* (2013.01); *A61B 2560/0214* (2013.01); *H02J 2007/0096* (2013.01); *H04B 5/0037* (2013.01)

(58) Field of Classification Search
CPC ............ A61B 5/002; A61B 2560/0204; A61B 2560/0214; A61B 2560/0219; H02J 50/20; H02J 50/05; H02J 50/10; H02J 7/025; H02J 50/80; H02J 2007/0096; G01R 31/3689
See application file for complete search history.

(56) References Cited

U.S. PATENT DOCUMENTS

| | | | |
|---|---|---|---|
| 8,280,476 B2 | 10/2012 | Jina | |
| 2004/0172222 A1* | 9/2004 | Simpson | G06F 19/3418 702/189 |
| 2005/0199494 A1 | 9/2005 | Say et al. | |
| 2007/0150019 A1* | 6/2007 | Youker | A61N 1/3787 607/29 |
| 2008/0167531 A1 | 7/2008 | McDermott | |
| 2008/0221555 A1 | 9/2008 | Sheppard et al. | |
| 2008/0242962 A1 | 10/2008 | Roesicke et al. | |
| 2009/0085768 A1* | 4/2009 | Patel | A61B 5/14532 340/870.05 |
| 2009/0171178 A1 | 7/2009 | He et al. | |
| 2009/0240128 A1 | 9/2009 | Mensinger et al. | |
| 2010/0324392 A1 | 12/2010 | Yee et al. | |
| 2011/0213225 A1* | 9/2011 | Bernstein | G06Q 50/22 600/309 |
| 2012/0283968 A1* | 11/2012 | Katsuki | A61B 5/1473 702/60 |
| 2012/0293340 A1 | 11/2012 | Chan | |
| 2013/0289372 A1 | 10/2013 | Imran | |
| 2015/0182153 A1 | 7/2015 | Feldman et al. | |

FOREIGN PATENT DOCUMENTS

| | | |
|---|---|---|
| EP | 1 611 838 B1 | 10/2012 |
| WO | WO 03/005891 A1 | 1/2003 |
| WO | WO 2008/083379 A1 | 7/2008 |
| WO | WO 2008/124597 A1 | 10/2008 |
| WO | WO 2010/091028 A1 | 8/2010 |
| WO | WO 2011/154372 A1 | 12/2011 |
| WO | WO 2012/007437 A1 | 1/2012 |
| WO | WO 2012/068393 A1 | 5/2012 |

OTHER PUBLICATIONS

International Standard ISO/IEC 14443-3; Identification cards—Contactless integrated circuit cards—Proximity cards—Part 3: Initialization and anticollision (Jun. 1, 2016) (72 pages).
International Standard ISO/IEC 14443-4; Identification cards—Contactless integrated circuit cards—Proximity cards —Part 4: Transmission protocol (Jun. 1, 2016) (62 pages).
International Standard ISO/IEC 14443-1; Identification cards—Contactless integrated circuit cards—Proximity cards—Part 1: Physical characteristics (Preview) (Mar. 15, 2016)(6 pages).
EP 15183461.1 Extended European Search Report dated Feb. 23, 2016 (11 pages).
International Standard ISO/IEC 15693-1 Identification cards—Contactless integrated circuit cards—Vicinity cards—Part 1: Physical characteristics (Oct. 1, 2010) (10 pages).
International Standard ISO/IEC 15693-3 Identification cards—Contactless integrated circuit cards—Vicinity cards—Part 3: Anticollision and transmission protocol (Apr. 15, 2009)(50 pages).
International Standard ISO/IEC 15693-2 Identification cards—Contactless integrated circuit cards—Vicinity cards—Part 2: Air interface and initialization (Dec. 15, 2006) (22 pages).

* cited by examiner

SENSOR MODULE AND KIT FOR DETERMINING AN ANALYTE CONCENTRATION

CROSS REFERENCE TO RELATED APPLICATIONS

This application claims priority from European Patent Application No. 15 183 461.1 filed on Sep. 2, 2015, the disclosure of which is incorporated herein by reference.

BACKGROUND

1. Technical Field

The present disclosure relates to a sensor module, a kit and a method for determining a concentration of at least one analyte in a body fluid of a user. The devices and methods according to the disclosed embodiments may mainly be used for long-term monitoring of an analyte concentration in a body fluid, such as for long-term monitoring of a blood glucose level or of the concentration of one or more other types of analytes in a body fluid. The disclosed embodiments may be applied both, in the field of home care, as well as in the field of professional care, such as in hospitals. Other applications are also feasible.

2. Description of the Related Art

Monitoring certain bodily functions, more particularly monitoring one or more concentrations of certain analytes, plays an important role in the prevention and treatment of various diseases.

In addition to so-called spot measurements, in which a sample of a bodily fluid is taken from a user in a targeted fashion and examined with respect to the analyte concentration, continuous measurements are increasingly becoming established. Thus, in the recent past, continuous measuring of glucose in the interstitial tissue (also referred to as continuous monitoring, CM), for example, has been established as another important method for managing, monitoring and controlling a diabetes state.

In the process, the active sensor region is applied directly to the measurement site, which is generally arranged in the interstitial tissue, and, for example, converts glucose into electrical charge by using an enzyme (e.g. glucose oxidase, GOD), which charge is related to the glucose concentration and can be used as a measurement variable. Examples of such transcutaneous measurement systems are described in U.S. Pat. No. 6,360,888 B1 and in US 2008/0242962 A1.

Hence, current continuous monitoring systems are generally transcutaneous systems. This means that the actual sensor or at least a measuring portion of the sensor is arranged under the skin of the user. However, an evaluation and control part of the system (also referred to as a patch) is generally situated outside of the body of the user, that is to say outside of the human or animal body. In the process, the sensor is generally applied using an insertion instrument, which is likewise described in U.S. Pat. No. 6,360,888 B1 in an exemplary fashion. Other types of insertion instruments are also known.

WO 2008/124597 A1 discloses an analyte sensing device having one or more sensing electrodes. The analyte sensing device comprises a main body configured to reside on the skin of an individual when in use, the main body having one or more electrical components. The analyte sensing device further comprises an analyte sensing electrode extending substantially perpendicularly from and electrically coupled to the main body. The analyte sensing electrode is configured for insertion into the skin of the individual.

Transcutaneous sensor systems typically imply a large number of technical challenges. Thus, a first challenge resides in the fact that the lifetime of a sensor is limited. A sensor is generally worn for approximately one week. After that, influences such as enzymes being used up and/or a sealing off in the body generally reduce the sensitivity of the sensor, or it is expected that the sensor fails. Increasing the duration of wear is an area of current research. However, this means that the sensor and, optionally, components directly connected to the former such as an insertion needle, are often designed as replaceable components. Accordingly, the sensor and optionally further replaceable components generally constitute a so-called disposable. By contrast, in many cases, the evaluation and control part of the system is reused. Accordingly, this evaluation and control part is often embodied as a so-called reusable.

The separation between a disposable and a reusable, however, generally implies additional technical challenges. Thus, a significant challenge resides in the fact that the sensitive interface between the disposable part and the reusable part is susceptible to contamination, which might lead to deterioration of the quality of the electrical measurements. Further, electrochemical systems typically are based on a potentiostatic measurement principle and, generally, may sustain very small electrical currents only, since, with larger electrical currents, electrode deterioration may occur. The deterioration of measurement signals may occur gradually, over a long time period and may be detected electronically only with a large technical effort. These technical challenges are increased by the fact that the reusable part is generally handled by the end-user or patient rather than by trained medical staff.

A further challenge of continuous monitoring systems resides in the fact that these systems require a constant effort to keep the volume of the sensor system or at least the part of the sensor system worn on the user's body at a low level, in order to increase the comfort of wearing. Thus, the functionality of the sensor system generally has to be kept at a low level, in order to avoid voluminous components such as displays or user interfaces. This reduction of functionality, however, often leads to the fact that remote resources have to be used, such as for data evaluation and/or communication with the user. In this case, however, unidirectional or bidirectional exchange of data and information between the sensor and the remote device becomes an issue. Several systems for managing this communication are known in the art.

WO 2012/068393 A1, US 2010/0324392 A1, WO 2012/007437 A1, WO 2011/154372 A1, WO 03/005891 A1, U.S. Pat. No. 8,280,476 B2, EP 1 611 838 B1, WO 2008/083379 A1, EP 1 850 226 A1, US 2005/0199494 A1, and US 2009/0240128 A1 disclose various concepts for analyte monitoring systems, including concepts for a modular setup of the systems and various concepts for data transmission of measuring data.

A further challenge in many concepts for continuous monitoring of one or more analytes resides in an energy supply of the various components of the systems. In U.S. Pat. No. 7,756,561 B2, a method and an apparatus for providing a disposable power supply source integrated into the housing of the transmitter unit mount that is placed on the skin of the patient and configured to receive the transmitter unit are disclosed. The transmitter unit mount is configured to be disposable with the analyte sensor so that power supply providing power to the transmitter unit is also replaced. The transmitter unit may include a rechargeable battery that is recharged by the power supply unit of the transmitter unit mount when the transmitter is mounted to the transmitter unit mount. A similar concept is disclosed in US 2009/0171178 A1.

In WO 2010/091028 A1, methods and devices to monitor an analyte in a body fluid are provided. Therein, an on-body patch device is used which may communicate with a reader device via RF. Inter alia, it is disclosed that the reader device may be configured to provide RF power to the on-body patch device. In response, the on-body patch device may be configured to generate an output signal, e.g. an RF signal, and transmit it to the reader device which includes, among others, data indicating the glucose measurement.

Still, despite the progress that has been made with the above-mentioned concepts, some major technical problems and challenges remain. Thus, still, functionality and energy concepts of the sensor systems will have to be improved, in order to increase usability of insurgent sensors and to improve the user's comfort by reducing the frequency of replacing the insurgent sensor. Since, with improved sensor chemicals, the actual sensor lifetime steadily increases, there remains a demand for improved energy concepts for long-term analyte monitoring systems.

SUMMARY

The present disclosure provides a concept for determination of a concentration of at least one analyte in a body fluid of a user which avoids the above-mentioned problems of known systems and devices. Specifically, devices and methods are disclosed which address the demand for improved energy supply concepts in analyte monitoring systems. Such devices and methods include a sensor module, a kit and a method. Various features of the embodiments may be realized in an isolated fashion or in any reasonable combination.

Without restricting further possible applications, the embodiments disclosed in the present application will be described in the following text with reference to blood-glucose monitoring. However, additionally or alternatively, the present disclosure can also be applied to other types of analytes.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, as used in the following, the terms "preferably", "more preferably", "particularly", "more particularly", "specifically", "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

In a first aspect of the present disclosure, a sensor module for determining a concentration of at least one analyte in a body fluid of a user is disclosed. The sensor module includes at least one sensor element adapted to determine the concentration of the analyte, wherein the sensor element is at least partly implantable into a body tissue of the user; at least one control device connected to the sensor element, wherein the control device includes at least one data collection device adapted to collect measurement data acquired by using the sensor element, wherein the control device further includes at least one wireless near-field communication device adapted to transmit measurement data, wherein the control device further includes a rechargeable energy storage device, and wherein the control device is adapted to transmit at least one demand for recharging the rechargeable energy storage device via the near-field communication device.

In a further aspect of the present disclosure, a kit for determining a concentration of at least one analyte in a body fluid of a user is disclosed. The kit includes the sensor module according to one or more of the embodiments described herein, and at least one further module, wherein the at least one further module is adapted to receive the at least one demand for recharging the rechargeable energy storage device.

As used herein, a "kit" is an assembly of a plurality of components, wherein the components each may function and may be handled independently from each other, wherein the components of the kit may interact to perform a common function. Thus, the kit may comprise a plurality of components, wherein each component may be handled individually, independent from the other components and may perform at least one function independently, wherein, further, all components or groups of components comprising at least two of the components may be combined, such as by physically connecting these components, in order to perform a common function implying functionality from the connected components.

The kit comprises the above-mentioned components, i.e. the at least one sensor module and the at least one further module. As used herein, the term "further module" generally may refer to an arbitrary module of the kit which may be handled independently from the sensor module. Preferably, the at least one further module is adapted to fulfill at least one function, as will be outlined in further detail below, such as an analytical function and/or an electrical function and/or a medical function.

As outlined above, the components of the kit may be handled independently from each other, i.e. each of the components may have at least one state in which the respective component is not mechanically connected to any other component. Additionally, as will be outlined in further detail below, the components of the kit have at least one state in which these components are connected to at least one other component, thereby mechanically interacting with this component. Further, each of the components of the kit may have an individual function, such as a measurement function, a data storage function and a data transmission function, which may be exerted independently from the presence of other components. Further, in the connected state, an interaction function may occur, which will be outlined in further detail below.

As further used herein, the term "determining a concentration" relates to a process of generating at least one representative result or a plurality of representative results indicating the concentration of the analyte in the body fluid.

As further used herein, the term "analyte" may refer to an arbitrary element, component or compound which may be present in a body fluid and the concentration of which may be of interest for a user. Preferably, the analyte may be or may comprise an arbitrary chemical substance or chemical compound which may take part in the metabolism of the user, such as at least one metabolite. As an example, the at least one analyte may be selected from the group consisting of glucose, cholesterol, triglycerides, lactate. Additionally or alternatively, however, other types of analytes may be used and/or any combination of analytes may be determined.

Generally, an arbitrary type of body fluid may be used. Preferably, the body fluid is a body fluid which is present in a body tissue of the user, such as in the interstitial tissue. Thus, as an example, the body fluid may be selected from the group consisting of blood and interstitial fluid. However, additionally or alternatively, one or more other types of body fluids may be used. The body fluid generally may be contained in a body tissue. Thus, generally, the concentration of the at least one analyte in the body fluid of the user may preferably be determined in vivo.

As generally used within the present invention, the term "user" may refer to a human being or an animal, independent from the fact that the human being or animal, respectively, may be in a healthy condition or may suffer from one or more diseases. As an example, the user may be a human being or an animal suffering from diabetes. However, additionally or alternatively, the invention may be applied to other types of users.

The sensor module comprises at least one sensor element adapted to determine the concentration of the analyte, wherein the sensor element is at least partly implantable into a body tissue of the user. The sensor module further includes at least one control device connected to the sensor element, wherein the control device includes at least one data collection device adapted to collect measurement data acquired by using the sensor element. The control device further includes at least one wireless near-field communication device adapted to transmit measurement data.

As used herein, the term "sensor module" generally refers to a unit, which may be handled as one entity, comprising the at least one sensor element, preferably precisely one sensor element, and the at least one control device, preferably precisely one control device.

As further used herein, the term "sensor element" generally refers to an arbitrary element which is adapted to determine the concentration of the analyte. Thus, as will be outlined in further detail below, the at least one sensor element preferably includes at least one sensor material, wherein the sensor material is adapted to perform at least one detectable reaction in the presence of the analyte. The sensor material preferably may be a sensor material selected from the group consisting of: an optical sensor material, wherein the optical sensor material is adapted to perform at least one optically detectable detection reaction in the presence of the analyte; an electrochemical sensor material, wherein the electrochemical sensor material is adapted to perform at least one electrically detectable detection reaction in the presence of the analyte, such as an electrically detectable redox reaction.

The sensor element preferably may include at least one flexible substrate, such as a flexible substrate having an elongated shape, wherein the flexible substrate may extend into the body tissue of the user. Specifically in case the at least one sensor element is an electrochemical sensor element, the sensor element preferably has two or more electrodes applied to the substrate, such as at least one working electrode and at least one further electrode, such as at least one counter electrode and/or at least one reference electrode. For potential examples of the sensor element, reference may be made to the prior art documents listed above, such as to the continuous transcutaneous measurement systems as described in U.S. Pat. No. 6,360,888 B1 or in US 2008/0242962 A1. Additionally or alternatively, other types of sensor elements may be used.

As further used herein, the term "at least partly implantable into a body tissue of the user" refers to the fact that the sensor element is adapted to have appropriate dimensions to be inserted into the body tissue of the user, such as into subcutaneous tissue, and, further, that the sensor element is biocompatible in order to remain in the body tissue for an elongated time period, such as for several days or even several weeks or several months. Thus, as an example, the sensor element or at least the implantable part of the sensor element may have a biocompatible coating, such as at least one semipermeable membrane, which prevents the sensor material from migrating into the body tissue and, still, which is permeable to the at least one analyte. Thus, as outlined above, the sensor element may comprise at least one flexible substrate with two or more electrodes deposited on the substrate, wherein at least one of the electrodes is coated by a semipermeable membrane. Thus, the electrodes each may comprise a conductive electrode pad, wherein at least one of these electrode pads is coated with the sensor material, functioning as a working electrode. The conductive electrode pads may be contacted by two or more contact leads.

The term "implant" refers to the fact that the sensor element may be inserted fully or partially into the body tissue. Thus, in the following, the terms "implant" and "insert" will be used as synonyms. Generally, during implantation and/or during use of the sensor element, the sensor element may fully or partially penetrate the skin of the user. Thus, the sensor element preferably may be embodied as a transcutaneous sensor element.

As used herein, the term "control device" generally refers to an arbitrary element which is adapted to acquire measurement data by using the data collection device. A "data collection device" generally may refer to an arbitrary device adapted for collecting and preferably storing data such as measurement data. Thus, the data collection device generally may include at least one data storage device such as at least one volatile and/or at least one non-volatile data storage element. The control device preferably may rest on a skin surface of the user, wherein the sensor element preferably extends from the control device into the body tissue of the user. The control device preferably may have a closed housing, as will be outlined in further detail below. The data collection device preferably may have at least one electronic component connected to the sensor element, preferably electrically connected to the sensor element. As will be outlined in further detail below, the connection may be a permanent connection or a releasable and/or reversible connection.

The control device may be adapted to be placed on a skin or an out-of-body surface of the user. Thus, the control device may be an external, extracorporal control device. Alternatively, the control device may fully or partially be inserted into the body tissue of the user, too, since, as will be outlined in further detail below, the present invention allows for rendering the control device rather small such that an insertion or implantation of the control device into the body tissue creates less discomfort for the user as compared to conventional control devices. This is mainly due to the fact that, due to the possibility of recharging the rechargeable energy storage device, the rechargeable energy storage device may be rendered rather small as compared to conventional sensor modules.

Preferably, specifically in case the sensor element is an electrochemical sensor element, the data collection device may comprise at least one potentiostatic measurement device such as at least one potentiostat. Generally, the data collection device may comprise at least one amplifier having a high input resistance, such as an input resistance of at least 1 MΩ, preferably at least 100 MΩ or even at least 1 GΩ, such as 10 GΩ. Generally, for potential embodiments of the control device and the data collection device, reference may be made to the electronics measurement setups as disclosed in U.S. Pat. No. 6,360,888 B1 or in US 2008/0242962 A1. However, as will be outlined in further detail below, the at least one control device preferably is a unitary control device which is not subdivided into a reusable and a disposable part. Apart from this fact, the measurement setups as disclosed in these documents may be transferred to the embodiments described herein. Other embodiments are feasible.

As further used within the present disclosure, the term "measurement data" refers to arbitrary data acquired by using the sensor element, indicative of the analyte concentration. The measurement data may specifically include a plurality of measurement values acquired at subsequent points in time, such as over a time period of several hours, several days, several weeks or even several months. The measurement data preferably may be acquired in an analogue or digital electronic format. The measurement data further may be processed or pre-processed within the control device, such as by applying at least one evaluation or pre-evaluation algorithm to the measurement data. Thus, as an example, at least one algorithm may be applied to the measurement data, wherein the at least one algorithm transforms primary measurement data acquired by using the sensor element into secondary measurement data indicating the concentration of the analyte in the body fluid, such as by applying a known or predetermined relationship between the primary measurement data and the analyte concentration to the primary measurement data, thereby generating secondary measurement data. Here and in the following, no difference will be made between primary measurement data, i.e. the measurement data directly acquired by using the sensor element, and secondary measurement data which are generated by applying one or more evaluation or pre-evaluation algorithms to the primary measurement data.

As used herein, the term "near-field communication", abbreviated by NFC, generally refers to a wireless transfer of data over short distances of up to 10 cm, generally having a low data transfer rate, such as a data transfer rate of no more than 424 kBit/s. As an example, the near-field communication may follow a passive standard, i.e. a standard in which one of the communication partners is a passive component which only answers communication requests received from the other partner, such as the standard defined in ISO 14443 and/or ISO 15693. Thus, preferably, the near-field communication may be a RFID communication, wherein, preferably, the wireless near-field communication device of the control device is the passive element of the RFID communication. Additionally or alternatively, other types of near-field communication may be used, such as near-field communications in which both partners of the communication are active partners, i.e. partners which may both send and receive communication requests.

The near-field communication device preferably may include at least one communication component adapted to perform the near-field communication. Thus, as an example, the near-field communication device may include at least one antenna. As an example, the near-field communication device may include at least one RFID antenna, such as at least one RFID coil. The near-field communication device may further include additional components, such as one or more communication ICs or the like.

The transmission of the measurement data by using the wireless near-field communication device may take place to one or more other elements, such as one or more other elements of the kit, as will be outlined in further detail below. Thus, the communication of the measurement data by using near-field communication may take place to one or more of a data reader module, a data transmission module, an optional alarm module and a portable data management device, which will be explained in further detail below.

As outlined above, the control device includes at least one rechargeable energy storage device. As used herein, generally, a "rechargeable energy storage device" refers to an arbitrary device which is adapted to store energy, preferably electrical energy, in a rechargeable fashion, such that the energy storage device, once it has provided its energy fully or partially to other parts of the control device, may fully or partially be recharged. As an example, the rechargeable energy storage device may include one or more rechargeable electrical energy storage devices, such as one or more of: at least one rechargeable battery; at least one rechargeable accumulator; at least one rechargeable capacitor, such as at least one rechargeable supercapacitor, more preferably at least one rechargeable capacitor having an electrical capacitance of at least 100 µF, more preferably a rechargeable capacitor having an electrical capacitance of at least 1 mF; at least one rechargeable electrical energy storage device having an electrical capacity for providing an electrical energy of 0.001 A·h to 3 A·h, more preferably for providing electrical energy of 0.01 A·h to 1 A·h.

As outlined above, the control device is adapted to transmit at least one demand for recharging the rechargeable energy storage device via the near-field communication device. Thus, generally, the control device may be adapted to transmit at least one item of information regarding a status of charge of the rechargeable energy storage device via the near-field communication device, such as at least one item of information on an actual charge and/or an actual voltage of the at least one rechargeable energy storage device. The at least one item of information, as an example, may be an arbitrary item of information from which a status of charge of the at least one rechargeable energy storage device may be deduced. Thus, as used herein, a "demand for recharging" generally may be or may include an arbitrary item of information regarding one or both of a status of charge of the at least one rechargeable energy storage and/or an information indicating that a recharging of the rechargeable energy storage device is necessary in order to maintain an operation of the sensor module. A "demand", as used in the context of the present disclosure, thus generally may refer to an arbitrary item of information from which a necessity for recharging the rechargeable energy storage device may be deduced.

Thus, generally, the sensor module and the kit may be adapted to provide a concept of recharging on-demand for the rechargeable energy storage device. Consequently, the rechargeable energy storage device may be dimensioned smaller as compared to conventional analytical sensors, since the rechargeable energy storage device not necessarily has to provide electrical energy for the full duration of operation of the sensor module. Thus, the sensor module may be rendered small, with a relatively small energy storage device, and, if required, the energy storage device may be recharged on demand.

The control device specifically may be adapted to transmit a charging status of the rechargeable energy storage device via the near-field communication device. As will be outlined in further detail below, an addressee of the charging status transmitted by the control device may be the at least one further module, such as the at least one data management device, the at least one data reader module, the at least one data transmission module, the at least one alarm module, the at least one dedicated recharging module or an arbitrary combination thereof. Other options are feasible.

In an embodiment, the control device itself may be adapted to indicate a charging status of the rechargeable energy storage device to a user, preferably by one or more of a visual indicator, an acoustic indicator or a vibrational indicator. Alternatively, however, the control device itself may be completely passive, without having any indicators such as acoustic, visual or vibrational indicators. The indication of a charging status and/or of a necessity for recharging the rechargeable energy storage may thus specifically may be performed by one or more further modules, such as by the at least one data management device. Thereby, by rendering the control device and the sensor module without any indicators of its own, the sensor module and the control device may be rendered specifically small.

The control device may be adapted to recharge the rechargeable energy storage device with electrical energy provided externally to the sensor module. This recharging specifically may take place in a wireless and/or contactless fashion. Thus, as an example, the sensor module may be adapted such that the electrical energy provided externally to the sensor module may be provided in one or more of the following ways: a capacitive coupling, an inductive coupling, a magnetic coupling, an electromagnetic transmission. Thus, as an example, the kit may contain, besides the at least one sensor module, at least one further module adapted for providing electrical energy to the at least one rechargeable energy storage device in a contactless and/or wireless fashion, such as via one or more of a capacitive coupling, an inductive coupling, a magnetic coupling or an electromagnetic transmission. Other ways of recharging, however, are feasible.

In case the recharging on-demand actually fails, the sensor module may be adapted to switch to at least one emergency mode. Thus, as an example, the sensor module may be adapted to switch to at least one sleep mode in case a remaining energy level inside the at least one rechargeable energy storage device falls below one or more predetermined thresholds. Additionally or alternatively, the sensor module may further include at least one emergency power supply, which may be adapted to provide an amount of energy to the control device and/or the rechargeable energy storage device in case a regular recharging is momentarily not feasible. Thus, as an example, the at least one optional emergency power supply may be adapted to supply electrical energy to the control device and/or the rechargeable energy storage device in case, after transmitting at least one demand for recharging the rechargeable energy storage device, no recharging has taken place. Additionally or alternatively, the at least one emergency power supply may be available at all times The at least one emergency power supply may be embodied in various ways. Thus, generally, the at least one emergency power supply may contain one or more energy storage devices. Additionally or alternatively, however, the at least one emergency power supply may comprise one or more energy converters adapted for converting energy into electrical energy usable by the control device and/or chargeable into the at least one rechargeable energy storage device. Thus, as an example, the emergency power supply includes at least one of the following: a power generator adapted for transforming a mechanical energy into electrical energy, preferably a piezo-electric power generator and/or a magneto-electric power generator, such as a power generator based on Eddie currents; a power generator manually operable by a user; an energy harvesting device for harvesting energy from a surrounding environment of the sensor module and for transforming the harvested energy into electrical energy.

As outlined above, the kit specifically may be embodied such that the at least one further module or, in case a plurality of further modules is provided, at least one of the further modules is adapted to provide energy to the rechargeable energy storage device. The at least one further module specifically may be adapted to provide electrical energy to the rechargeable energy storage device in a wireless and/or contactless fashion. The at least one further module may be adapted to provide electrical energy to the rechargeable energy storage device in one or more of the following ways: a capacitive coupling, an inductive coupling, a magnetic coupling; an electromagnetic transmission.

As outlined above, the at least one further module may include a variety of modules having various functions. Thus, generally, the modular setup of the kit may increase a functionality of the kit, while still keeping the volume of the actual sensor module low. Thus, as an example, the at least one further module may include one or more of the following further modules: the at least one portable data management device; at least one data transmission module; the at least one data reader module; the at least one alarm module; the at least one dedicated recharging module.

Thus, as an example, the at least one further module may include at least one portable data management device, wherein the portable data management device is adapted to directly or indirectly receive the measurement data and to at least partially display data on at least one display. As an example, the at least one data management device may include a portable computer, such as a smartphone, a palmtop computer or any other portable computing device. The data management device may be adapted to bring the demand for recharging the rechargeable energy storage device to a user's attention, such as in one or more of a visual fashion, an acoustic fashion or a vibrational fashion. Thus, as an example, the data management device may be adapted to provide at least one of a visual indication, such as a display of an appropriate message, and/or an acoustic indication, such as a warning sound or a voice message, and/or a vibrational indication, such as a vibrational alarm, to a user, in order to indicate to the user that a recharging of the rechargeable energy storage device is required. The user may thus be encouraged and/or instructed to perform one or more recharging steps, such as one or more recharging steps indicated on a display of the data management device, as will be explained in further detail below.

The data management device may be adapted to indicate to a user at least one way of recharging the rechargeable energy storage device. The indication, as an example, may take place in a verbal fashion and/or by using one or more pictograms. The data management device, as an example, may be adapted to indicate to the user that at least one recharging module has to be brought into at least one recharging position with respect to the sensor module. As used herein, a "recharging module" generally may refer to at least one module of the kit which is adapted for recharging the at least one rechargeable energy storage device. As an example, the at least one recharging module may be or may include one or more of the above-mentioned modules, such as the at least one data management device, the at least one data transmission module, the data reader module or the alarm module. Alternatively, the at least one recharging module may be or may include at least one dedicated recharging module, i.e. at least one module the sole purpose of which or the main purpose of which is the recharging of the at least one rechargeable energy storage device. The at least one dedicated recharging module, as outlined above, may be part of the at least one further module.

As outlined above, the at least one further module may include at least one data reader module adapted to receive measurement data transmitted by the sensor module via wireless near-field communication. The data reader module may include at least one data storage device and may be adapted to store the measurement data.

As used herein, the term "data reader module" generally refers to a unit which may be handled as a unitary element and which is adapted to store the measurement data. For the purpose of receiving measurement data transmitted by the sensor module via wireless near-field communication, the data reader module may include at least one near-field communication device. Thus, as an example, a near-field communication device according to one or more of the above-mentioned standards may be used. As an example, the near-field communication device of the data reader module may be an active device, whereas the wireless near-field communication device of the control device of the sensor module may be a passive communication device. However, other options are possible, such as active communication devices in both components. The near-field communication device of the data reader module preferably may include at least one antenna, such as at least one RFID antenna.

The data storage device may be an arbitrary storage device adapted to store the measurement data. A volatile and/or non-volatile data storage device may be used. As an example, the storage device, also referred to as a memory device or a memory element, may include one or more storage chips and/or other types of memory devices, wherein both volatile and non-volatile memory devices may be employed.

As further outlined above, the at least one further module may, additionally or alternatively, include at least one data transmission module adapted to receive measurement data transmitted by the sensor module via wireless near-field communication. The data transmission module may include at least one wireless far-field communication device, wherein the wireless far-field communication device is adapted to transmit at least part of the measurement data to an external device via wireless far-field communication.

The kit further includes at least one data transmission module adapted to receive measurement data transmitted by the sensor module via wireless near-field communication. The data transmission module includes at least one wireless far-field communication device, wherein the wireless far-field communication device is adapted to transmit at least part of the measurement data to an external device via wireless far-field communication.

As used herein, the term "data transmission module" generally refers to an arbitrary unit which may be handled as a unitary element which is adapted to receive the measurement data via wireless near-field communication from the sensor module and which is adapted to transmit at least part of the measurement data to an external device via wireless far-field communication. Thus, the data transmission module may include at least one wireless near-field communication device adapted to communicate with the wireless near-field communication device of the control device of the sensor module. As an example, the near-field communication device may be an active near-field communication device, whereas the near-field communication device of the control device of the sensor module may be a passive communication device. However, other options are possible, such as active communication devices in both elements.

As used herein, the term "wireless far-field communication" generally refers to a wireless communication adapted to transmit data over long distances, such as distances of more than 10 cm. As an example, the wireless far-field communication may be an arbitrary long-range communication using electromagnetic waves in the radio frequency range, i.e. may be a radio communication. Thus, as an example, the wireless far-field communication device of the data transmission module may include at least one radio module, having at least one radio antenna, for transmitting the measurement data via radio transmission to the at least one external device.

As used herein, the term "external device" may be an arbitrary device independent from the data transmission module and the sensor module which is adapted to receive the measurement data via wireless far-field communication. The at least one external device may be part of the kit or may be independent from the kit. As an example, the at least one external device may be a portable device having the capability of communicating via wireless far-field communication, such as a hand-held computer and/or a smartphone. Thus, as an example, the above-mentioned data management device itself may be the external device or may form part of the external device. Additionally or alternatively, the at least one optional external device may be another device, independent from the components of the kit. As outlined above, the external device specifically may be the data management device, such that the data may be transmitted via near-field communication from the sensor module to the data transmission device and, thereafter, from the data transmission device to the data management device via far-field communication. Other embodiments are feasible.

The at least one further module may, additionally or alternatively, include at least one alarm module adapted to receive data transmitted by the sensor module via wireless near-field communication. The data transmitted by the sensor module may contain one or both of measurement data or alarm instructions. The alarm module may be adapted to generate at least one alarm signal in response to the data transmitted by the sensor module.

Thus, as an example, the alarm module may include at least one wireless near-field communication device, preferably an active near-field communication device, which may communicate with the near-field communication device of the control device of the sensor element. As an example, the wireless near-field communication device may include at least one antenna.

As outlined above, the data transmitted by the sensor module may contain alarm instructions. Thus, the alarm module may be a passive alarm module which simply is adapted for generating an alarm signal in response to alarm instructions received by the sensor module. Thus, the sensor module may be adapted to determine whether at least one alarm condition is fulfilled, such as in case one or more thresholds of analyte concentration are exceeded, and, if this is the case, may transmit alarm instructions to the alarm module. The alarm module may generate an alarm signal in response to these alarm instructions.

Additionally or alternatively, the alarm module may provide, at least partially or to a certain extent, an intelligence of its own, such as by providing one or more processors or other types of data processing devices. Thus, as outlined above, the data transmitted by the sensor module may contain measurement data. The alarm module may be adapted to evaluate the measurement data and to determine whether at least one alarm condition is fulfilled and to provide at least one alarm signal in case the at least one alarm condition is fulfilled. Thus, the alarm module may include at least one data processing device, such as at least one processor and/or microcontroller, adapted to perform at least one evaluation algorithm, wherein the evaluation algorithm is adapted to evaluate the measurement data received by the sensor module and to determine whether the alarm condition is fulfilled or not. Thus, as an example, the at least one alarm condition may include at least one comparison with one or more threshold levels, wherein, as an example, an alarm condition may be fulfilled in case a specific threshold level is reached and/or exceeded. Thus, as an example, an alarm condition may be fulfilled in case a maximum tolerable blood glucose level is exceeded. The alarm module may be flexible with regard to evaluating the measurement data. Thus, the alarm module may be a programmable alarm module. As an example, a user may select and/or adjust one or more thresholds to be used in the alarm condition, such as one or more thresholds for analyte concentrations. For this purpose, such as for programming the alarm module, the alarm module may include one or more wireless and/or wire-bound interfaces, such as one or more interfaces adapted to be connected to a personal computer, a smartphone or another type of controller. Via one or more of these interfaces, a programming of the alarm module may be feasible.

The at least one alarm signal, as outlined in further detail below, may be generated by at least one alarm device. The at least one alarm signal preferably may be selected from the group consisting of an acoustic alarm signal, an optical alarm signal and a vibrational alarm signal. However, other types of alarm signals may be generated, such as alarm signals transmitted via wireless or wire-bound data transmission to at least one external device, such as to at least one medical computer.

As outlined above, the alarm module preferably may include at least one data evaluation device, also referred to as a data processing element. Preferably, the at least one data processing element may have a software code stored therein, with program means for subjecting the measurement data to the at least one alarm condition. Thus, by using the program means, the above-mentioned threshold comparisons may be performed. Additionally or alternatively, as outlined above, the alarm module simply may be a passive alarm module adapted for receiving one or more alarm instructions from the sensor module and to provide an alarm signal in response to this at least one alarm instruction.

As outlined above, the alarm signal preferably may be selected from the group consisting of an acoustic alarm signal, an optical alarm signal and a vibrational alarm signal. However, additionally or alternatively, other types of alarm signals may be generated, such as one or more electronic alarm signals, e.g. alarm signals transmitted via wire-bound and/or wireless signal transmission, such as radio-transmission, to an external device, such as an external computer and/or a smartphone. Thus, generally, the alarm signal may be an alarm signal which may be recognized by a human user, such as healthcare personal or the user of the kit, and/or an electronic alarm signal which may be recognized as such by a machine.

The sensor module may include a sensor module mechanical interface for reversibly coupling the sensor module to the at least one further module. As used herein, the term "sensor module mechanical interface" generally refers to an arbitrary element or a combination of elements of the sensor module which is adapted to interact with at least one mechanical interface of a further module in order to generate a mechanical connection between the sensor module and the other element. Generally, the sensor module mechanical interface may comprise an arbitrary type of element or combination of elements which may be used for coupling to the further module, such as one or more elements selected from the group consisting of: a protrusion, a rim, a hook, a depression, a groove. Other types of connection elements may be used additionally or alternatively. The at least one further module may comprise at least one corresponding mechanical interface adapted to reversibly engage the sensor module, such as to the optional sensor module mechanical interface, thereby generating a fixed spatial relationship between the sensor module and the at least one further module. Alternatively, for near-field communication with the sensor module, the at least one further module simply may be brought into close proximity with the at least one sensor module in order to enable a near-field communication between the sensor module and the at least one further module.

As outlined above, the at least one further module may include at least one dedicated recharging module adapted to recharge the rechargeable energy storage device. The at least one dedicated recharging module may include at least one rechargeable energy storage. As an example, the at least one rechargeable energy storage may be or may include an electrical energy storage, such as one or more of a battery, an accumulator, a capacitor or any other type of electrical energy storage. Preferably, electrical energy storage of the dedicated recharging module may be rechargeable, too. Preferably, the electrical energy storage of the dedicated recharging module may have a capacity of at least 0.1 A·h, at least 0.3 A·h, or at least 0.5 A·h. Thus, as an example, the electrical energy storage of the dedicated recharging module may have a capacity of 0.1 A·h to 2.0 A·h, such as 0.3 A·h to 1.0 A·h.

In another embodiment, the at least one further module may include at least two further modules, including at least one data transmission module, such as defined above, adapted to receive measurement data transmitted by the sensor module via wireless near-field communication, wherein the data transmission module includes at least one wireless far-field communication device, wherein the wireless far-field communication device is adapted to transmit at least part of the measurement data to an external device via wireless far-field communication; and at least one portable data management device, such as defined above, wherein the portable data management device is adapted to directly or indirectly receive the measurement data and to at least partially display data on at least one display; wherein the data transmission module is adapted to receive the at least one demand for recharging the rechargeable energy storage device and to transmit the demand to the portable data management device, preferably via wireless far-field communication, wherein the data management device is adapted to bring the demand for recharging the rechargeable energy storage device to a user's attention.

For further optional details, such as for details regarding embodiments of the portable data management device and/or for options regarding bringing the demand for recharging to the user's attention, reference may be made to one or more of the embodiments described above.

The configuration of the kit may be adapted to the actual needs of the measurement situation. Thus, the weight and the volume of the sensor module may be kept at a low level. The sensor module, as an example, may have a volume below 7 $cm^3$, more preferably a volume below 5 $cm^3$, below 2.5 $cm^3$, or even below 2 $cm^3$ or below 1.5 $cm^3$. Specifically, the sensor module and, more preferably, the control device of the sensor module, may be embodied such that no voluminous components are present, such as voluminous wireless far-field communication components and/or voluminous data memories. Further, the sensor module may be embodied without any wire-bound data interfaces, such as without any mechanical plugs. Consequently, the sensor module may be embodied as a cheap, small, low-level component which simply may be adapted to acquire measurement data and transmit the measurement data via wireless near-field communication. Still, despite the fact that the sensor module may be kept at a low resource level and, thus, at a low level with regard to weight and volume, the kit may provide a full functionality of modern analytical systems, such as by providing the capability of far-field data transmission to data handling devices such as one or more computers for evaluating the measurement data. Further, the data reader module may be used for data storage and/or data transfer, in the fashion of modern memory sticks, such as USB memory sticks.

As outlined above, the at least one further module specifically may include at least one portable data management device. The portable data management device may be adapted to directly or indirectly receive the measurement data and to at least partially display the measurement data. As used herein, the term "at least partially display" generally refers to the fact that one or more of the full measurement data, a part thereof or data or information derived from the measurement data are displayed by using at least one display device, such as a matrix display. As an example, measurement curves derived from the measurement data may be displayed on a screen, such as an LCD screen or any other type of display device.

The portable data management device may further be adapted to perform at least one data evaluation algorithm. Thus, the portable data management device may further be adapted to apply the at least one data evaluation algorithm on the measurement data or a part thereof, such as in order to derive at least one evaluation result. As an example, an analyte concentration, mean values, a health condition or other types of evaluation results may be derived by using the evaluation algorithm.

Thus, generally, the data management device may simply be a display device adapted for displaying data, only, whereas the sensor module and/or the data transmission module may provide the capability of data evaluation. Alternatively, the data management device may provide an intelligence of its own, such as by providing one or more data processing devices adapted to apply the at least one data evaluation algorithm on the measurement data.

As used herein, the term "portable" generally refers to the fact that the data management device may be carried by a user, such as by hand. Thus, the data management device may be a hand-held data management device. As an example, the data management device may have a weight of less than 1 kg, preferably a weight of less than 500 g and, more preferably, a weight of less than 300 g. Further, the portable data management device may have a volume of preferably less than 1000 $cm^3$, more preferably of less than 120 $cm^3$ or even less than 60 $cm^3$.

Generally, the term "data management device", as used herein, refers to a device adapted to handle measurement data, such as by storing the measurement data and/or subjecting the measurement data to at least one data evaluation algorithm. Thus, as an example, the data management device may have at least one algorithm for displaying the measurement data, such as by displaying the measurement data on a display device, thereby displaying one or more measurement curves. Additionally or alternatively, averaging algorithms may be applied to the measurement data and/or one or more algorithms adapted to give medical advice to the user. Further, the portable data management device may comprise one or more databases, such as for storing and/or comparing measurement data.

The portable data management device may be adapted to directly or indirectly receive the measurement data. As used herein, the term "directly receiving the measurement data" refers to the option that the portable data management device directly receives the measurement data from the sensor module, such as by wireless near-field communication. The term "indirectly receiving the measurement data" generally refers to the option that at least one intermediate device may be used for transmitting the measurement data fully or in part to the portable data measurement device. Thus, the at least one data transmission module may be used for transmitting the measurement data fully or in part to the portable data management device via wireless far-field communication. These options will be outlined in further detail below.

In addition to displaying the measurement data and, optionally, applying at least one evaluation algorithm to the measurement data, the data management device may further be adapted to perform one or more additional actions. Thus, as an example, the data management device may be adapted to initiate one or more further actions, such as to automatically shut off a medication pump, specifically an insulin pump, in response to the measurement data. Thus, as an example, the data evaluation algorithm may be adapted to determine whether one or more conditions are fulfilled, on the basis of the measurement data, and, in response to this determination, may initiate one or more actions such as shutting off the medication pump.

Further, the data management device may be adapted to send data and/or instructions to one or more other devices. Thus, as an example, the data management device may be adapted to communicate with the sensor module. As an example, the data management device may be adapted to transmit data to the sensor module, preferably via near-field communication. As an example, the data management device may be adapted to transmit calibration data to the sensor module. Additionally or alternatively, the data management device may be adapted to transmit specific alarm conditions and/or alarm adjustments which may individually be adjustable by a user.

The portable data management device may comprise at least one device selected from the group consisting of: a portable computer; a smartphone; a watch; a medication pump, such as an insulin pump or a part thereof, such as a medication pump controller; a hand-held device for determining a concentration of the analyte in a body fluid. In case the portable data management device comprises a hand-held device for determining a concentration of the analyte in a body fluid, the hand-held device generally may comprise an arbitrary meter for determining the analyte concentration. Thus, as an example, the hand-held device may be adapted to use at least one test element having at least one test field, preferably a test strip or a test tape, wherein a sample of the body fluid may be applicable to the test field. Thus, as opposed to the implantable sensor element of the sensor module, the hand-held device may be a spot meter adapted to perform an in vitro analysis of the body fluid. Thus, as an example, the hand-held device may be a hand-held glucose monitoring device using one or more test strips or one or more test tapes, wherein a sample of the body fluid, such as a droplet of blood and/or interstitial fluid, may be applied to the test strip or test tape, in order to determine the concentration of the analyte in the body fluid, such as the blood glucose concentration. Thus, the hand-held device generally may comprise a commercially available blood glucose meter. Additionally or alternatively, other types of hand-held devices for determining the analyte concentration may be used.

The data management device further may include one or more user interfaces allowing for a user to insert commands. Thus, the data management device may include one or more keys for inserting data and/or commands. The data management device additionally or alternatively may include at least one data processing element adapted to apply at least one data processing algorithm to the measurement data. Thus, the data processing element may be adapted to apply at least one averaging algorithm and/or at least one evaluation algorithm to the measurement data, wherein, as an example, one or more types of information may be derived from the measurement data, such as information regarding the measurement data exceeding certain levels of the analyte concentration. Further, additionally or alternatively, the data management device may include one or more databases for storing the measurement data.

The measurement device may be adapted to receive measurement data from the data transmission module via wireless far-field communication. Thus, as an example, the data management device may include one or more far-field communication components, such as one or more radio components. Additionally or alternatively, the data management device may be adapted to receive measurement data from the data transmission module via other ways of communication.

The data management device may further be adapted to receive measurement data directly from the sensor module via wireless near-field communication. Thus, the data management device may include one or more wireless near-field communication devices. Thus, as an example, many handheld devices such as modern smartphones include near-field communication devices, such as for reading RFID tags. Thus, as an example, the data management device may include one or more RFID readers to receive measurement data via RFID communication from the sensor module.

The data management device may further include at least one display element adapted to display a plurality of measurement data. Thus, the display element may include an active or passive display, such as a matrix display. Thus, the display element may be adapted to display measurement curves comprising a plurality of measurement data. Thus, the measurement device may be adapted to display a time development of the measurement data.

The sensor module preferably may be a disposable sensor module. Thus, as an example, the sensor module may be embodied such that the sensor module may be disposed as an entity. The sensor module may include a housing, which, preferably, may not be opened in a non-destructive fashion. Thus, preferably, the housing of the sensor module is a unitary piece containing all components of the control device, including the data collection device and the wireless near-field communication device as cheap, single-use components. A kit according to the present disclosure may include a plurality of exchangeable sensor modules.

Contrarily, the at least one further module may be embodied as one or more reusable units. Thus, preferably, the at least one further module and may include at least one rechargeable and/or exchangeable energy storage, such as at least one rechargeable and/or exchangeable battery and/or a rechargeable accumulator. In case an exchangeable energy storage is provided, preferably, the at least one further module comprises a housing which may be opened in a non-destructive way, in order to exchange the exchangeable energy storage. In case a rechargeable energy storage is provided, the further module may comprise a recharging device, which may be embodied as a wire-bound recharging device such as a plug and/or as a wireless charging device, such as an inductive recharging device.

In a further aspect of the present disclosure, a method for determining a concentration of at least one analyte in a body fluid of a user is disclosed. The method may include the steps described hereinafter. The method steps may be performed in the given order or in a different order. Further, one or more or even all of the method steps may be performed once or more than once or even repeatedly. The method may further include additional method steps which are not listed.

The method includes the use of one or both of the sensor module, such as according to one or more of the embodiments disclosed above or disclosed in further detail below, and/or of the kit, such as according to one or more of the embodiments disclosed above or disclosed in further detail below.

The method may further include transmitting at least one demand for recharging the rechargeable energy storage device of the sensor module via the near-field communication device of the sensor module. The method may further include at least one step of fully or partially recharging the at least one rechargeable energy storage device of the sensor module with electrical energy provided externally to the sensor module. For further optional details, reference may be made to the disclosure of the sensor module and/or the kit as given above and/or as given in further detail below.

The sensor module, the kit and the method according to the present disclosure provide a large number of advantages over known devices for determining an analyte concentration, such as continuous monitoring glucose sensors. Thus, the sensor module may be embodied as a very small module, having the analyte sensor and, as an example, a small, button-like control device on the skin surface of the user. The control device, as an example, may be mounted to the skin of the user by using an adhesive, such as an adhesive tape. Still, by using the flexible energy concept as proposed within the present disclosure, a sufficient time for operation and storage of the control device may be provided, due to the possibility of recharging the rechargeable energy storage device. Thus, as an example, the duration of operation of the sensor module may be limited by a test chemical or sensor chemical of the sensor element rather than by the energy content of the rechargeable energy storage device. Further, a data transfer rate and a mode of data transfer may be chosen according to the requirements of the kit and are not a limiting factor for the duration of operation of the sensor module any longer, also due to the possibility of recharging the at least one rechargeable energy storage device.

Further, the kit may be embodied to perform a mode of reading on demand. Thus, a data transfer of measurement data from the sensor module, directly or via the at least one data transmission module, to the data management device may take place on demand, such as initiated by the user. This mode generally requires a lower energy supply as compared to a mode of online monitoring, in which the sensor module permanently sends measurement data.

The sensor module does not necessarily have to be capable of storing an energy content for a storage and a period of operation, such as for seven days. Contrarily, the at least one rechargeable energy storage device may contain a lower energy content, and may be recharged on demand. Consequently, the at least one rechargeable energy storage device may be chosen at a smaller volume, and, consequently, the at least one sensor module, which may be embodied as a disposable sensor module, may be constructed smaller and at lower cost. Energy reserves and an over-dimensioning are not required any longer.

The energy management concept specifically may be managed by the data management device. Thus, the data management device, which may also be referred to as a "controller", obtains information on a status of charge of the at least one rechargeable energy storage device of the sensor module. This information may be transmitted in one step or a plurality of steps, i.e. directly or via one or intermediate steps, from the sensor module to the data management device. Thus, as an example, a near-field communication may take place from the sensor module to the at least one data transmission module, and, therefrom, to the at least one data management device. Alternatively, a direct near-field communication may take place between the sensor module and the data management device.

Subsequently, the data management device may provide appropriate commands for recharging the at least one rechargeable energy storage device of the sensor module. As an example, appropriate commands for recharging may be transmitted to one or more recharging modules, which may be one or more dedicated recharging modules and/or which may be one or more modules which actually are mainly adapted for performing different purposes.

Thus, as an example, the at least one further module as mentioned above may contain a dedicated recharging module having a rechargeable energy storage, such as a rechargeable accumulator. The dedicated recharging module may be coupled to the at least one sensor module for recharging the at least one rechargeable energy storage device of the sensor module. The coupling may take place via at least one mechanical interface and/or via simply bringing the at least one dedicated recharging module into close proximity with the sensor module. A successful finishing of the recharging may be signalized to the user. Similarly, a remaining energy content of the dedicated recharging module may be signalized to the user, such as via one or more of a visual indication, an acoustic indication or a vibrational indication.

Additionally or alternatively, the recharging module may make use of a data transmission module, such as a radio transmission module. This data transmission module may be used as a recharging module and may be used for recharging the at least one rechargeable energy storage device of the sensor module. Again, for this purpose, the data transmission module may be coupled to the at least one sensor module or may simply be brought into close proximity with the sensor module. During recharging, the data transmission module may fully or partially energize the sensor module, in order to save energy during recharging of the at least one rechargeable energy storage device and in order to provide energy for operation of the sensor module during recharging.

Further, in addition to the above-mentioned recharging concepts, the at least one data management device itself may be used as a recharging module. In this concept, the data management device, with its energy storage, may be used for recharging the rechargeable energy storage device of the sensor module. Again, for this purpose, the data management device may either be coupled to the sensor module or may be brought into close proximity with the sensor module during recharging.

For transferring energy from the at least one recharging module, various concepts are feasible. Thus, as an example, for recharging, the near-field communication may be used. Thus, as outlined above, the sensor module contains the at least one wireless near-field communication device. This at least one wireless near-field communication device itself may also be used for recharging the rechargeable energy storage device of the sensor module.

Additionally or alternatively, other concepts of wireless energy transfer are feasible. Thus, as an example, the recharging module may inductively transfer energy to the sensor module. As an example, one or more of an oscillator, a rectifier or an inverter may be used for transforming a direct current within the recharging module into an alternating current, for inductively recharging the rechargeable energy storage device of the sensor module. Within the sensor module, a rectification from an alternating current into a direct current may take place. This energizing concept is generally known from electric toothbrushes.

Additionally or alternatively, a capacitive energy transfer may take place. Thus, as an example, the recharging module may be adapted for capacitively coupling energy into the sensor module. The energy requirements for maintaining the functionality of the control device of the sensor module generally are rather low.

Further, as outlined above, the present energy concept may include an emergency energizing. Thus, as an example, as an emergency alternative, an emergency power supply may be provided within the sensor module. As an example, a piezo-electric charge generation within the sensor module may take place, initiated by the patient. As an example, the patient may induce pressure and/or movement in one or more piezo-electric elements, such as by hand. The piezo-electric energy may be used for at least partially recharging the rechargeable energy storage device.

Additionally or alternatively, the at least one emergency power supply may be based on eddie currents. As an example, the patient, preferably manually, may induce a mechanical movement of one or more parts of the sensor module, such as one or more parts containing a magnet. By inducing these movements, eddie currents and, thereby, electrical charges may be generated and may be used for at least partially recharging the rechargeable energy storage device of the sensor module.

The energy concept according to the present disclosure generally increases the flexibility of the sensor module and the overall kit for analyte monitoring. Thus, generally, the varying time of the sensor module as well as the measuring modi generally may be embodied independent from the actual energy source of the sensor module.

The sensor module, which preferably may be embodied as a "button sensor", having a button-shaped control device and a sensor element protruding therefrom, may communicate its charging status, directly or indirectly, via near-field communication to the data management device. The data management device, in turn, may send an appropriate recharging command to at least one recharging module, if the energy of the rechargeable energy storage device of the sensor module turns out to be low. As outlined above, various concepts for embodiments of the recharging module may be feasible. Thus, generally, the at least one data management device and/or the at least one recharging module may be considered as "at least one further module" which generally receives information regarding a status of charge of the at least one rechargeable energy storage device of the sensor module and may take appropriate measures for recharging the rechargeable energy storage device, with the user's help or automatically.

Thus, according to the present disclosure, various embodiments for the architecture of the recharging module are feasible, for the energy transfer and for emergency supply functions.

The at least one rechargeable energy storage device, as an example, may contain printed batteries and/or an additional module with printed batteries. Further, the at least one optional emergency power supply, as discussed above, may make use of one or more energy harvesting concepts, as generally known in the art. Thus, as an example, movement, temperature, pressure or other types of external influences may be used and may be transformed into energy usable by the emergency power supply.

As outlined above, the at least one sensor module of the kit is adapted for communicating with at least one further module of the kit, via near-field communication. As outlined above, the at least one further module, as an example, may include one or more of the following: the above-mentioned data management device; the above-mentioned data transmission module; the above-mentioned data reader module; the above-mentioned alarm module; and the above-mentioned dedicated recharging module.

Instead of using the at least one dedicated recharging module, the sole or main purpose of which is the recharging of the rechargeable energy storage device, one or more of the data management device, the data transmission module, the data reader module or the alarm module may also be used as recharging modules, since, generally, all of these modules will imply one or more energy storage functions, capable of sharing energy with the rechargeable energy storage device of the sensor module.

In case a separate, dedicated recharging module is used, this dedicated recharging module may contain a rechargeable accumulator which may be coupled, preferably wirelessly, to the sensor module, in order to recharge the at least one rechargeable energy storage device of the sensor module. Additionally or alternatively, as outlined above, the at least one data transmission module, which specifically may be a radio module, may be used as a recharging module. As outlined above, this data transmission module typically provides a rechargeable accumulator and may be used for reloading or even substituting the energy storage device of the sensor module. Again, additionally or alternatively, the data management device may be adapted to recharge the sensor module with its rechargeable energy storage, such as via NFC or RF communication. In this regard, reference may be made to WO 2010/091028 A1 and the energy transmission via RF as disclosed therein. This concept of energy transmission may also be used in the context of the present energy concept.

Summarizing the findings of the present invention, the following embodiments are preferred. Still, other embodiments are feasible.

Embodiment 1: A sensor module for determining a concentration of at least one analyte in a body fluid of a user that includes (a) at least one sensor element adapted to determine the concentration of the analyte, wherein the sensor element is at least partly implantable into a body tissue of the user; (b) at least one control device connected to the sensor element, wherein the control device includes at least one data collection device adapted to collect measurement data acquired by using the sensor element, wherein the control device further includes at least one wireless near-field communication device adapted to transmit measurement data, wherein the control device further includes a rechargeable energy storage device, and wherein the control device is adapted to transmit at least one demand for recharging the rechargeable energy storage device via the near-field communication device.

Embodiment 2: The sensor module according to the preceding embodiment, wherein the control device is adapted to transmit a charging status of the rechargeable energy storage device via the near-field communication device.

Embodiment 3: The sensor module according to any one of the two preceding embodiments, wherein the control device is adapted to indicate a charging status of the rechargeable energy storage device to a user, preferably by one or more of a visual indicator, an acoustic indicator or a vibrational indicator.

Embodiment 4: The sensor module according to any one of the preceding embodiments, wherein the control device is adapted to recharge the rechargeable energy storage device with electrical energy provided externally to the sensor module.

Embodiment 5: The sensor module according to the preceding embodiment, wherein the sensor module is adapted such that the electrical energy provided externally to the sensor module may be provided wirelessly in a contactless fashion.

Embodiment 6: The sensor module according to any one of the two preceding embodiments, wherein the sensor module is adapted such that the electrical energy provided externally to the sensor module may be provided in one or more of the following ways: a capacitive coupling, an inductive coupling, a magnetic coupling, an electromagnetic transmission.

Embodiment 7: The sensor module according to any one of the preceding embodiments, wherein the sensor module further comprises at least one emergency power supply, wherein the emergency power supply is adapted to provide an amount of energy to the rechargeable energy storage device in case a regular recharging is momentarily not feasible.

Embodiment 8: The sensor module according to the preceding embodiment, wherein the emergency power supply comprises at least one of the following: a power generator adapted for transforming a mechanical energy into electrical energy, preferably a piezo-electric power generator and/or a magneto-electric power generator, more preferably a power generator manually operable by a user; an energy harvesting device for harvesting energy from a surrounding environment of the sensor module and for transforming the harvested energy into electrical energy.

Embodiment 9: A kit for determining a concentration of at least one analyte in a body fluid of a user, wherein the kit includes the sensor module according to any one of the preceding embodiments, and at least one further module, wherein the at least one further module is adapted to receive the at least one demand for recharging the rechargeable energy storage device.

Embodiment 10: The kit according to the preceding embodiment, wherein the at least one further module is adapted to provide energy to the rechargeable energy storage device.

Embodiment 11: The kit according to the preceding embodiment, wherein the at least one further module is adapted to provide electrical energy to the rechargeable energy storage device in a contactless fashion.

Embodiment 12: The kit according to any one of the two preceding embodiments, wherein the at least one further module is adapted to provide electrical energy to the rechargeable energy storage device in one or more of the following ways: a capacitive coupling, an inductive coupling, a magnetic coupling; an electromagnetic transmission.

Embodiment 13: The kit according to any one of the preceding embodiments referring to a kit, wherein the at least one further module includes at least one portable data management device, wherein the portable data management device is adapted to directly or indirectly receive the measurement data and to at least partially display data on at least one display.

Embodiment 14: The kit according to the preceding embodiment, wherein the portable data management device is adapted to bring the demand for recharging the rechargeable energy storage device to a user's attention.

Embodiment 15: The kit according to the preceding embodiment, wherein the portable data management device is adapted to bring the demand for recharging the rechargeable energy storage device to the user's attention in one or more of a visual fashion, an acoustic fashion or a vibrational fashion.

Embodiment 16: The kit according to any one of the three preceding embodiments, wherein the portable data management device is adapted to indicate to a user at least one way of recharging the rechargeable energy storage device.

Embodiment 17: The kit according to the preceding embodiment, wherein the portable data management device is adapted to indicate to the user that at least one recharging module has to be brought into at least one recharging position with respect to the sensor module.

Embodiment 18: The kit according to any one of the preceding embodiments referring to a kit, wherein the at least one further module includes at least one data reader module adapted to receive measurement data transmitted by the sensor module via wireless near-field communication, wherein the data reader module comprises at least one data storage device and is adapted to store the measurement data.

Embodiment 19: The kit according to any one of the preceding embodiments referring to a kit, wherein the at least one further module comprises at least one data transmission module adapted to receive measurement data transmitted by the sensor module via wireless near-field communication, wherein the data transmission module comprises at least one wireless far-field communication device, wherein the wireless far-field communication device is adapted to transmit at least part of the measurement data to an external device via wireless far-field communication.

Embodiment 20: The kit according to any one of the preceding embodiments referring to a kit, wherein the at least one further module includes at least one alarm module adapted to receive data transmitted by the sensor module via wireless near-field communication, wherein the data transmitted by the sensor module contain one or both of measurement data or alarm instructions.

Embodiment 21: The kit according to any one of the preceding embodiments referring to a kit, wherein the at least one further module includes at least one dedicated recharging module adapted to recharge the rechargeable energy storage device.

Embodiment 22: The kit according to the preceding embodiment, wherein the at least one dedicated recharging module includes at least one rechargeable energy storage.

Embodiment 23: The kit according to any one of the preceding embodiments referring to a kit, wherein the at least one further module includes: at least one data transmission module adapted to receive measurement data transmitted by the sensor module via wireless near-field communication, wherein the data transmission module includes at least one wireless far-field communication device, wherein the wireless far-field communication device is adapted to transmit at least part of the measurement data to an external device via wireless far-field communication; and at least one portable data management device, wherein the portable data management device is adapted to directly or indirectly receive the measurement data and to at least partially display data on at least one display; wherein the data transmission module is adapted to receive the at least one demand for recharging the rechargeable energy storage device and to transmit the demand to the portable data management device, wherein the data management device is adapted to bring the demand for recharging the rechargeable energy storage device to a user's attention.

Embodiment 24: The kit according to any one of the preceding embodiments referring to a kit, wherein the sensor module includes a sensor module mechanical interface for reversibly coupling the sensor module to the at least one further module.

Embodiment 25: A method for determining a concentration of at least one analyte in a body fluid of a user, the method includes a use of one or both of the sensor module according to any one of the preceding embodiments referring to a sensor module or a kit according to any one of the preceding embodiments referring to a kit.

Embodiment 26: The method according to the preceding embodiment, wherein the method further includes transmitting at least one demand for recharging the rechargeable energy storage device of the sensor module via the near-field communication device of the sensor module.

Embodiment 27: The method according to the preceding embodiment, wherein the method further includes at least one step of fully or partially recharging the at least one rechargeable energy storage device of the sensor module with electrical energy provided externally to the sensor module.

Further optional features and embodiments of the invention will be disclosed in more detail in the subsequent description of preferred embodiments. Therein, the respective optional features may be realized in an isolated fashion as well as in any arbitrary feasible combination, as the skilled person will realize. The scope of the invention is not restricted by the preferred embodiments. The embodiments are schematically depicted in the Figures.

BRIEF DESCRIPTION OF THE DRAWINGS

The above mentioned and other features of this invention, and the manner of attaining them, will become more apparent and the invention itself will be better understood by reference to the following description of embodiments of the invention taken in conjunction with the accompanying drawings, wherein.

Corresponding reference characters indicate corresponding parts or functionally comparable elements throughout the several views. Although the exemplification set out herein illustrates embodiments of the invention, in several forms, the embodiments disclosed below are not intended to be exhaustive or to be construed as limiting the scope of the invention to the precise forms disclosed.

DETAILED DESCRIPTION

Figure 1:
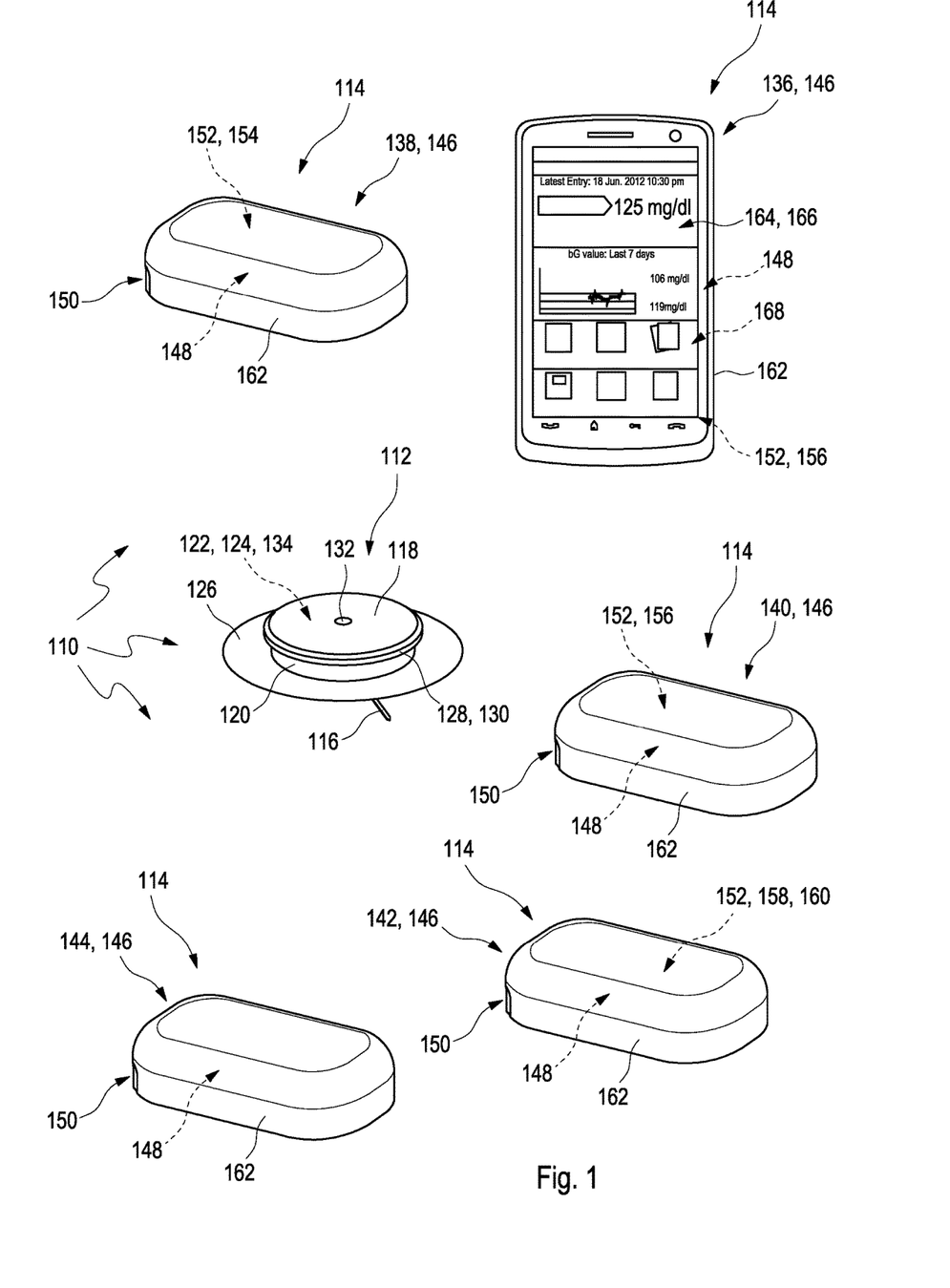
FIG. 1 shows an overview over an exemplary embodiment of a kit.

In FIG. 1, an exemplary embodiment of a kit 110 for determining a concentration of at least one analyte in a body fluid is disclosed. The kit comprises at least one sensor module 112 and at least one further module 114. In this exemplary embodiment of the kit 110, five optional types of further modules 114 are depicted which will be explained in further detail below. It shall be noted that, however, an arbitrary combination of the at least one sensor module 112 and one or more of the further modules 114 as depicted in FIG. 1 is also feasible.

The sensor module 112 comprises at least one sensor element 116 adapted to be at least partially implanted into a body tissue of the user. For exemplary embodiments of the sensor element 116, reference may be made to one or more of the prior art documents listed above. Thus, as an example, the sensor element 116 may be or may comprise at least one electrochemical sensor element, having at least one working electrode and at least one counter electrode, for electrochemically determining the concentration of the at least one analyte in the body fluid. Further, in order to be implantable into the body tissue of the user, besides having appropriate dimensions, the sensor element 116 may comprise one or more biocompatible coatings, such as one or more biocompatible membranes, in order to enhance biocompatibility of the implanted sensor element 116.

The sensor element 116 is connected to at least one control device 118 which, for example, may be encapsulated by a housing 120. The control device 118, as will be outlined in further detail below, may comprise at least one data collection device 122 and at least one wireless near-field communication device 124. For exemplary embodiments of these components, reference may be made to the above-mentioned prior art documents. Thus, as an example, the data collection device 122 may comprise one or more data storage devices, such as one or more volatile and/or non-volatile data collection devices. Further, the at least one wireless near-field communication device 124 may comprise one or more electronic components for near-field communication, as the skilled person will know.

The sensor module 112 may further include at least one self-adhesive patch 126 adapted to mount the sensor module 112 to a skin surface of the user.

The sensor module 112 may further include a sensor module mechanical interface 128. In this specific embodiment, for example, the sensor module mechanical interface 128 may include a circumferential protruding rim 130 which may be part of the housing 120, as depicted in FIG. 1, or which may be attached to the housing 120. It shall be noted, however, that the sensor module mechanical interface 128 is an optional part and that the at least one further module 114 may as well simply be held in close proximity to the sensor module 112 for near-field communication and/or for recharging. The sensor module 112, as depicted in FIG. 1, may have a rotational symmetry and, preferably, may have a volume of less than 2 cm$^3$. Further, the housing 120 may have a central opening 132 through which an insertion tool for inserting the sensor element 116 into the body tissue may penetrate the housing 120.

The sensor module 112 further comprises at least one rechargeable energy storage device 134. The at least one rechargeable energy storage device 134 may be adapted for supplying electrical energy to the control device 118 of the sensor module 112. As an example, the at least one rechargeable energy storage device 134 may be or may include at least one rechargeable battery and/or at least one rechargeable accumulator and/or at least one capacitor or supercapacitor. The at least one sensor module 112 may be adapted for wirelessly recharging the rechargeable energy storage device 134, such as by one or more of an inductive coupling, a capacitive coupling, magnetic coupling or electromagnetic radiation.

As outlined above, the kit 110 further includes the at least one further module 114. In the exemplary embodiment shown in FIG. 1, as an example, five types of possible further modules 114 are disclosed. Thus, the at least one further module 114 may comprise one or more of a data management device 136, a data reader module 138, a data transmission module 140, an alarm module 142 or a dedicated recharging module 144. As will be outlined in further detail below, the main or even sole purpose of the dedicated recharging module 144 is a recharging of the rechargeable energy storage device 134 of the sensor module 112. Additionally or alternatively, one or more or even all of the other further modules 114 may act as recharging modules 146, since each of these further modules 114 may comprise one or more energy storage devices 148 which may provide energy, preferably electrical energy, to the sensor module 112 and the rechargeable energy storage device 134 of the sensor module 112.

Figure 3:
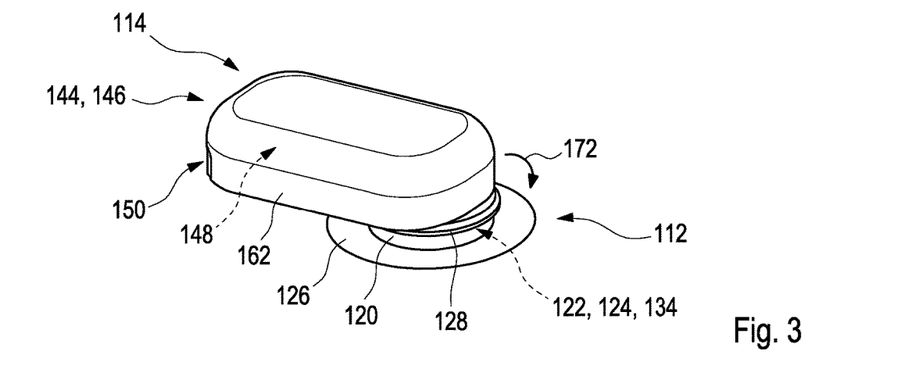
FIG. 3 shows a recharging of the sensor module.

The further modules 114, besides the data management device 136, may all optionally have a more or less similar geometric shape. Still, the further modules 114 may also be distinct, such as in terms of color and/or labeling or marking. The further modules 114 may, individually, have a mechanical interface 150 for coupling the respective further module 114 to the sensor module mechanical interface 128. Alternatively, however, as depicted in FIG. 3 below or as explained above, the further modules 114 as well may remain in an uncoupled state and simply may be brought into close proximity with the sensor module 112.

The data reader module 138 may be adapted to receive measurement data transmitted by the sensor module 112 via wireless near-field communication. For this purpose, the data reader module 138 may comprise a wireless near-field communication device 152. Similarly, the data transmission module 140 and, optionally, the alarm module 142 each may comprise one or more wireless near-field communication devices 152.

The data reader module 138 further includes at least one data storage device 154 and may be adapted to store measurement data transmitted by the sensor module 112 via wireless near-field communication. The at least one data transmission module 140 may include at least one wireless far-field communication device 156, such as at least one radio module. The wireless far-field communication device 156 may be adapted to transmit at least part of the measurement data to an external device via wireless far-field communication. As an example, a wireless near-field communication between the sensor module 112 and the data transmission module 140 may take place, and the data transmission module may be adapted to transmit the measurement data, fully or partially, via wireless far-field communication to at least one external device, such as to the at least one data management device 136 and/or to at least one further device, such as a computer, a computer network or a mobile device.

The alarm module 142 may include at least one data processing element 158 and may be adapted to evaluate the measurement data, in order to determine whether at least one alarm condition is fulfilled. Further, the alarm module 142 may be adapted to provide at least one alarm signal in case the at least one alarm condition is fulfilled. For this purpose, the alarm module 142 may include at least one alarm signal generator 160, such as an alarm signal generator 160 selected from the group consisting of an acoustic alarm signal generator, an optical alarm signal generator and a vibrational alarm signal generator. Thus, as an example, in case an alarm condition is determined to be fulfilled, the alarm module 142 may be adapted to vibrate and/or give an acoustic alarm signal and/or an optical alarm signal, such as an alarm sound and/or by providing repeated flashings of light and/or by changing an illumination state.

The further modules 114 may be designed as reusable components and, preferably, each may have a housing 162. As an example, the housings 162 may provide the option of being opened, in order to exchange a battery and/or another type of energy storage device 148. Additionally or alternatively, other ways of recharging and/or exchanging the energy storage devices 148 of the further modules 114 may be provided, such as in a wire-bound fashion and/or in a wireless fashion, such as by using a docking station or the like.

As depicted in the exemplary embodiment of FIG. 1, the kit 110 may be embodied such that the at least one further module 114 comprises the at least one data management device 136, preferably at least one portable data management device 136. The data management device 136 preferably may be a hand-held device, such as a hand-held computer and/or a hand-held communication device, such as a smartphone. As will be outlined in further detail below, the data management device 136 may, in one option, directly communicate with the sensor module 112 via wireless near-field communication, in order to receive measurement data. Additionally or alternatively, however, the data management device 136 may communicate with the data transmission module 140 via wireless far-field communication, in order to receive the measurement data from the sensor module 112 indirectly, via the data transmission module 140.

The data management device 136 may include at least one user interface 164, allowing for a user to insert commands and/or information. As indicated in FIG. 1, the user interface 164 may include, for example, a touchscreen. The data management device 136 may further, additionally or alternatively, comprise at least one display element 166, for displaying data and/or measurement results and/or additional information, such as information regarding a recharging procedure of the sensor module 112, as will be outlined in further detail below with reference to FIG. 2.

The data management device 136 may include at least one data processing element 168, such as at least one processor, adapted to apply at least one data processing algorithm to the measurement data. The data management device 136 may further include at least one data storage device and/or a memory, such as at least one database, for storing the measurement data. The data management device 136 may be adapted to apply at least one data processing algorithm to the measurement data. This data processing algorithm may imply a visualization of measurement data, such as a graphical display of measurement curves. Further, one or more items of additional information may be generated by evaluating the measurement data, such as by comparing the measurement data with one or more threshold values, in order to generate information on a medical status of the user.

For communicating via wireless near-field communication, the data management device 136 may optionally include at least one wireless near-field communication device 152. For wireless far-field communication, the data management device 136 may further include at least one wireless far-field communication device 156, as indicated in FIG. 1.

In the following, the specific interactions of the components of the kit 110 are disclosed in exemplary details. Thus, as indicated above, the sensor module 112, as depicted in FIG. 1, may be operated such that the sensor element 116 is at least partially implanted into a body tissue of the user. In this state or even in a state in which the sensor element 116 is not implanted, the sensor module 112 may communicate with one or more of the further modules 114 via wireless near-field communication, in order to transmit measurement data. Specifically, measurement data may be transferred to the data reader module 138 via wireless near-field communication. The data reader module 138 may be adapted to store the measurement data in the data storage device 154. At a later point in time, the data reader module 138 may fully or partially transfer the measurement data to another device, such as to the at least one data management device 136, and/or to another computer, such as a personal computer and/or a smartphone. The transfer may take place wirelessly and/or in a wire-bound fashion, such as via one or more interfaces not depicted in FIG. 1. Thus, as an example, the data reader module 138 may comprise a USB interface and/or another type of plug. Additionally or alternatively, a wireless transfer may take place, such as data transfer via infrared data transmission, Bluetooth or other types of wireless data transmission. Specifically, the data reader module 138 may be used in the same fashion as a USB data stick. The user, specifically the patient, may collect measurement data on a regular basis, by using the data reader module 138, and may transfer the measurement data to a medical supervisor, such as a doctor, by simply carrying the data reader module to the medical supervisor's office. Additionally or alternatively, the data reader module 132 may provide sufficient storage capability for storing measurement data over an elongated time period, such as over one week or several weeks.

The sensor module 112 may further transfer measurement data via wireless near-field communication to the at least one data transmission module 140, such as in a state in which the data transmission module 140 is in close proximity with the sensor module 112 and/or in which the data transmission module 140 is coupled to the sensor module 112. The data transmission module 140, thereafter, may transfer the measurement data, by using its wireless far-field communication device 156, to one or more external devices or other devices, such as to the data management device 136 and/or to another device, such as a computer, a computer network or a mobile device. As an example, the wireless far-field communication device 156 may be designed as a radio transmitter, a radio receiver and/or a radio transceiver.

As outlined above, the sensor module 112 comprises the at least one rechargeable energy storage device 134 which allows for operation of the control device 118 over a specific time period. The control device may further be adapted to transmit, via the near-field communication device 124, at least one demand for recharging the rechargeable energy storage device 134. The demand, which may also be referred to as a request for recharging and/or a status report on a status of charge of the rechargeable energy storage device 134, may be transferred to one or more of the further modules 114. Thus, as an example, the control device 118 may be adapted to transmit the at least one demand for recharging the rechargeable energy storage device 134 directly or indirectly to the data management device 136. This transmission is symbolically depicted in FIG. 2, wherein the near-field communication is denoted by reference number 170. Therein, the near-field communication 170 may take place directly between the sensor module 112 and the data management device 136. Additionally or alternatively, at least one intermediate station of transmission may be used. Thus, as an example, the data transmission module 140 may be used for receiving the demand for recharging the rechargeable energy storage device 134 and may transmit the demand to the data management device 136, by near-field communication and/or by other means of communication, such as wireless far-field communication. Thus, directly or indirectly, the request or demand for recharging the rechargeable energy storage device 134 is transmitted to the data management device 136.

Figure 2:
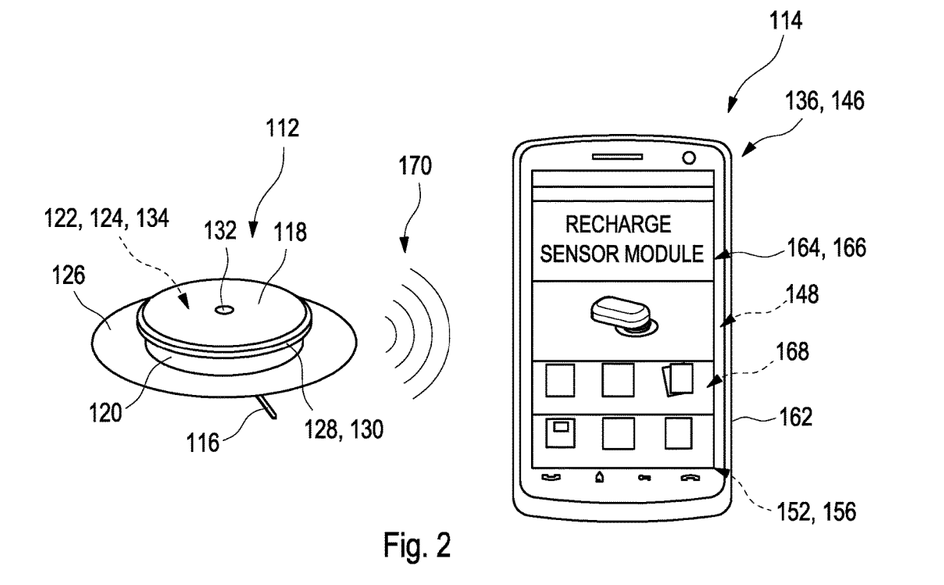
FIG. 2 shows, symbolically, a transmission of a demand for recharging from a sensor module to a data management module of the kit.

The data management device 136 may be adapted to initiate a recharging process. Thus, as an example, a processor of the data management device 136 may be adapted to evaluate the demand for recharging the rechargeable energy storage device 134. As an example, a processor of the data management device 136 may be adapted to compare at least one status information regarding a status of charge of the rechargeable energy storage device 134 with at least one threshold value, in order to recognize a need for recharging the rechargeable energy storage device 134. Additionally or alternatively, the information transmitted by the sensor module 112 may directly contain the information that the rechargeable energy storage device 134 has to be recharged.

The data management device 136 may be adapted, in case a need for recharging is detected, to take appropriate measures in order to recharge the rechargeable energy storage device 134. As an example and as depicted in FIG. 2, the display element 166 may indicate visual indications indicating the need for recharging the rechargeable energy storage device 134. Thus, as an example, verbal messages may be displayed. Additionally or alternatively, visual messages may be displayed which indicate at least one way of recharging the rechargeable energy storage device, such as by bringing one or more recharging modules 146 in a recharging position with respect to the sensor module 112. Both options are depicted symbolically in FIG. 2.

In FIG. 3, a recharging procedure, initiated by the data management device 136, is depicted. Thus, one or more recharging modules 146 may be brought into close proximity with the sensor module 112. For this purpose, the at least one recharging module 146 may simply be brought into close proximity with the sensor module 112 and/or may even be coupled to the sensor module 112, such as by coupling the mechanical interface 150 to the sensor module mechanical interface 128. As outlined above, the recharging module 146, as an example, may be the dedicated recharging module 144 and/or another type of further module 114. As an example, the data reader module 138, the data transmission module 140 or even the alarm module 142 may be used as recharging modules. Again, additionally or alternatively, the data reader module 138 itself may be used as a recharging module 146 for recharging the rechargeable energy storage device 134 of the sensor module 112.

In the recharging position shown in FIG. 3, energy may be transferred from the energy storage device 148 of the recharging module 146 into the rechargeable energy storage device 134 of the sensor module 112. The energy transfer, in FIG. 3, is symbolically depicted by reference number 172. Preferably, the recharging procedure and the energy transfer 172 may take place in a wireless fashion. Thus, as an example, the recharging and the energy transfer 172 may take place by one or more of an inductive coupling, a capacitive coupling, the near-field communication device 124 or any other type of electromagnetic coupling or electromagnetic radiation. As an example, the energy transfer 172 may take place by using one or more coils within the recharging module 146 and the sensor module 112, generating an inductive coupling. Additionally or alternatively, the recharging module 146 and the sensor module 112 each may contain one or more capacitors which may be coupled in a capacitive way, in order to capacitively transfer energy from the recharging module 146 to the sensor module 112. Additionally or alternatively, other types of transmitters, receivers or transceivers may be used for wirelessly transferring energy from the recharging module 146 to the sensor module 112.

Figure 4:
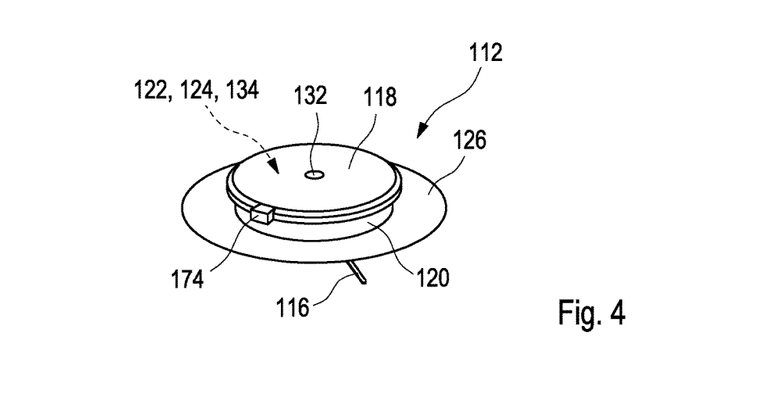
FIG. 4 shows an optional emergency power supply of the sensor module.

In FIG. 4, the option of an emergency power supply 174 of the sensor module 112 is symbolically depicted. Thus, as an example, in case a recharging of the rechargeable energy storage device 134 by the above-mentioned mechanism should turn out to be impossible momentarily, a user may manually recharge the rechargeable energy storage device 134 by using the emergency power supply. As an example, the emergency power supply 174 as depicted in FIG. 4 may comprise one or more buttons or levers on an outer side of the housing 120 of the sensor module 112. The user may manually operate this lever, in order to generate piezoelectric energy which, again, may be used to fully or partially recharge the rechargeable energy storage device 134.

It shall be noted that other means of emergency power supply 174 are feasible, such as energy harvesting methods and/or methods inducing eddie currents in order to recharge the rechargeable energy storage device 134.

LIST OF REFERENCE NUMBERS

110 kit for determining a concentration of at least one analyte in a body fluid
112 sensor module
114 further module
116 sensor element
118 control device
120 housing
122 data collection device
124 near-field communication device
126 self-adhesive patch
128 sensor module mechanical interface
130 rim
132 opening
134 rechargeable energy storage device
136 portable data management device
138 data reader module
140 data transmission module
142 alarm module
144 dedicated recharging module
146 recharging module
148 energy storage device 150 mechanical interface
152 wireless near-field communication device
154 data storage device
156 wireless far-field communication device
158 data processing element
160 alarm signal generator
162 housing
164 user interface
166 display element
168 data processing element
170 near-field communication
172 energy transfer
174 emergency power supply While this invention has been described as having an exemplary design, the present invention may be further modified within the spirit and scope of this disclosure. This application is therefore intended to cover any variations, uses, or adaptations of the invention using its general principles.

What is claimed is:

1. A sensor module for determining a concentration of at least one analyte in a body fluid of a user comprising:
   a. at least one sensor element having a limited life and adapted to determine the concentration of the analyte, wherein the sensor element is at least partly implantable into a body tissue of the user;
   b. at least one control device connected to the sensor element, wherein the control device comprises at least one data collection device adapted to collect measurement data acquired by using the sensor element,
   wherein the control device further comprises at least one wireless near-field communication device adapted to transmit measurement data,
   wherein the control device further comprises a rechargeable energy storage device, and wherein the control device is adapted to transmit at least one demand for recharging the rechargeable energy storage device via the near-field communication device; and
   wherein the sensor module is a single-use disposable module having a closed housing with the at least one control device and the rechargeable energy storage device disposed within the housing wherein the housing can only be opened in a destructive manner and wherein the rechargeable energy storage device must be recharged at least once to provide electrical energy to the sensor module for the full duration of the limited life of the sensor element.

2. The sensor module according to claim 1, wherein the control device is adapted to recharge the rechargeable energy storage device with electrical energy provided externally to the sensor module.

3. The sensor module according to claim 1, wherein the sensor module further comprises at least one emergency power supply, wherein the emergency power supply is adapted to provide an amount of energy to the rechargeable energy storage device in case a regular recharging is momentarily not feasible.

4. A kit for determining a concentration of at least one analyte in a body fluid of a user, the kit comprising:
   a plurality of sensor modules according to claim 1, and at least one further module, wherein the at least one further module is reusable and adapted to receive the at least one demand for recharging the rechargeable energy storage device from each of the plurality of sensor modules.

5. The kit according to claim 4, wherein the at least one further module is adapted to provide energy to the rechargeable energy storage device.

6. The kit according to claim 5, wherein the at least one further module is adapted to provide electrical energy to the rechargeable energy storage device in a contactless fashion.

7. The kit according to claim 4, wherein the at least one further module comprises at least one portable data management device, wherein the portable data management device is adapted to directly or indirectly receive the measurement data and to at least partially display data on at least one display.

8. The kit according to claim 7, wherein the portable data management device is adapted to bring the demand for recharging the rechargeable energy storage device to a user's attention.

9. The kit according to claim 7, wherein the portable data management device is adapted to indicate to a user at least one way of recharging the rechargeable energy storage device.

10. The kit according to claim 9, wherein the portable data management device is adapted to indicate to the user that at least one recharging module has to be brought into at least one recharging position with respect to the sensor module.

11. The kit according to claim 4, wherein the at least one further module comprises at least one data reader module adapted to receive measurement data transmitted by the sensor module via wireless near-field communication, wherein the data reader module comprises at least one data storage device and is adapted to store the measurement data.

12. The kit according to claim 4, wherein the at least one further module comprises at least one data transmission module adapted to receive measurement data transmitted by the sensor module via wireless near-field communication, wherein the data transmission module comprises at least one wireless far-field communication device, wherein the wireless far-field communication device is adapted to transmit at least part of the measurement data to an external device via wireless far-field communication.

13. The kit according to claim 4, wherein the at least one further module comprises at least one alarm module adapted to receive data transmitted by the sensor module via wireless near-field communication, wherein the data transmitted by the sensor module contain one or both of measurement data or alarm instructions.

14. The kit according to claim 4, wherein the at least one further module comprises at least one dedicated recharging module adapted to recharge the rechargeable energy storage device.

15. A method for determining a concentration of at least one analyte in a body fluid of a user, the method comprising a use of the sensor module according to claim 1 and transmitting at least one demand for recharging the rechargeable energy storage device of the sensor module via the near-field communication device of the sensor module.

16. A method for determining a concentration of at least one analyte in a body fluid of a user, the method comprising a use of the kit according to claim 4 and transmitting at least one demand for recharging the rechargeable energy storage device of the sensor module via the near-field communication device of the sensor module.

* * * * *